United States Patent
Buisman et al.

[19]
[11] Patent Number: 6,156,205
[45] Date of Patent: Dec. 5, 2000

[54] PROCESS FOR THE PURIFICATION OF GASES CONTAINING HYDROGEN SULPHIDE

[75] Inventors: Cees Jan Nico Buisman, Harich, Netherlands; Dimitri Yuri Sorokin, Moscow, Russian Federation; Joannes Gijsbrecht Kuenen, Delft, Netherlands; Albert Jozef Hendrik Janssen, Sneek, Netherlands; Lesley Anna Robertson, Den Haag, Netherlands

[73] Assignee: Paques Bio Systems B.V., Balk, Netherlands

[21] Appl. No.: 09/180,548

[22] PCT Filed: May 12, 1997

[86] PCT No.: PCT/NL97/00265

§ 371 Date: Jan. 25, 1999

§ 102(e) Date: Jan. 25, 1999

[87] PCT Pub. No.: WO97/43033

PCT Pub. Date: Nov. 20, 1997

[30] Foreign Application Priority Data

May 10, 1996 [EP] European Pat. Off. .............. 96201286

[51] Int. Cl.$^7$ ................................ C02F 3/34; B01D 19/00
[52] U.S. Cl. ........................... 210/620; 210/622; 95/156; 423/220; 423/243.11; 435/266
[58] Field of Search ..................................... 210/610, 611, 210/620–622; 435/266; 423/220, 243.01, 243.11; 95/156, 186

[56] References Cited

U.S. PATENT DOCUMENTS 1,832,325  11/1931  Rosenstein .
5,354,545  10/1994  Buisman .
5,366,633  11/1994  Buisman .
5,401,657   3/1995  Jones et al. .
5,480,550   1/1996  Sublette .
5,508,014   4/1996  Rai .
5,637,220   6/1997  Buisman .

FOREIGN PATENT DOCUMENTS 0 650 758     5/1995    European Pat. Off. .
8801009      11/1989    Netherlands .
WO 92/10270   6/1992    WIPO .
WO 94/29227  12/1994    WIPO .

OTHER PUBLICATIONS by Vedenina et al., "ATP synthesis by heterotrophic bacteria during the oxidation of thiosulfate to tetrathionate", *Chemical Abstracts Service*, Columbus, Ohio, 1993.

*Primary Examiner*—Duane Smith
*Assistant Examiner*—Fred Prince
*Attorney, Agent, or Firm*—Young & Thompson

[57] ABSTRACT

A process for scrubbing a gas containing hydrogen sulphide and/or carbonyl sulphide, in which the spent scrubbing liquid is treated with autotrophic sulphide-oxidizing bacteria capable of oxidizing at high pH, and elemental sulphur is obtained, the elemental sulphur is separated and the treated scrubbing liquid is recycled to the gas scrubbing step. Before recycling, the scrubbing liquid may further be treated with heterotrophic thiosulphate-oxidizing bacteria which produce polythionate which is useful for further enhancing the sulphide-scrubbing capacity of the scrubbing liquid.

19 Claims, 2 Drawing Sheets

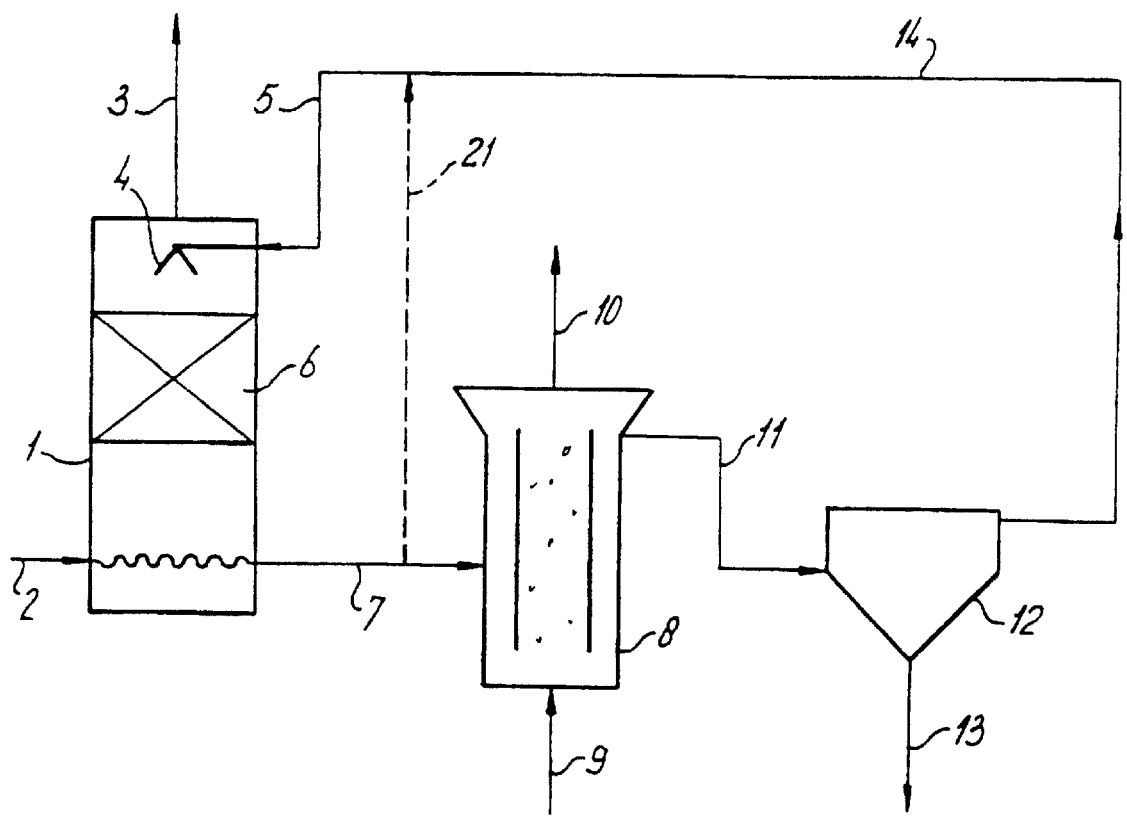

PROCESS FOR THE PURIFICATION OF GASES CONTAINING HYDROGEN SULPHIDE

CROSS REFERENCE TO RELATED APPLICATION

This is the 35 USC 371 National Stage application of International application PCT/NL97/00265 filed on May 12, 1997, which designated the United States of America.

FIELD OF THE INVENTION

The invention relates to a process for the purification of gas containing hydrogen sulphide and possibly other contaminants, in which process use is made of sulphide-oxidising bacteria.

BACKGROUND OF THE INVENTION

International Patent Application WO 92/10270 discloses a process for the purification of a gas containing hydrogen sulphide, in which the gas is scrubbed in a gas scrubber with an alkaline scrubbing liquid, the scrubbing liquid used is treated in an aerobic reactor with oxygen in the presence of sulphur-oxidising bacteria the effluent from the aerobic reactor is used again as scrubbing liquid and the elemental sulphur formed during the treatment with oxygen is separated from the effluent. The process is suitable for the removal of hydrogen sulphide ($H_2S$) and other reduced sulphur compounds, such as mercaptans and carbon disulphide, or for the removal of sulphur dioxide ($SO_2$). For $H_2S$ removal, the pH is kept between 8 and 9 by means of buffering compounds. The sulphur-oxidising bacteria used include the genera Thiobacillus and Thiomicrospira.

A disadvantage of this known process is that relatively large quantities of scrubbing liquid are necessary in order to absorb the hydrogen sulphide effectively. The known process is also unsuitable for the removal of other contaminants which may be present in addition to $H_2S$, such as carbonyl sulphide (COS).

SUMMARY OF THE INVENTION

It has now been found that biological conversion of sulphide to elemental sulphur can be performed at high pH using selected autotrophic sulphide-oxidising bacteria. As a result of the higher pH, the required quantity of scrubbing liquid is substantially reduced and the required equipment can therefore be smaller and less expensive. The new bacteria to be used according to the invention are effective at a pH above 9 up to about 11, in particular at a pH of 9.2 to 10.5. The bacteria to be used especially have a pH optimum above 9.0.

The biological oxidation of hydrogen sulphide and carbonyl sulphide using the autotrophic alkaliphilic bacteria predominantly results in the production of elemental sulphur, with some thiosulphate being formed as a byproduct.

It has further been found that thiosulphate can be converted to polythionate efficiently and with an increase in pH by a treatment in the presence of oxygen or a nitrogen oxide using thiosulphate-oxidising bacteria. Such thiosulphate-oxidising bacteria may include known sulphur-oxidisers, such as those of the genera Thiobacillus and Thiomicrospira, or heterotrophic bacteria. The term polythionate is used herein to comprise trithionate ($S_3O_6^{2-}$), tetrathionate ($S_4O_6^{2-}$), and possibly higher polythionate ($S_nO_6^{2-}$, n>4) species. The absorption of $H_2S$, COS (carbonyl sulphide) and other sulphur compounds by the scrubbing solution can be improved by using the solution containing the polythionate ions obtained in this way, with the result that these contaminants can be removed from gases more efficiently and with less scrubbing liquid. The process essentially yields only solid elemental sulphur. The optional bacterial thiosulphate-oxidising treatment can be performed simultaneously with the sulphide-oxidising treatment—if oxygen is used as the thiosulphate-oxidising agent—, but preferably the oxidation of thiosulphate is performed subsequently in a separate stage.

The process according to the invention is particularly suitable for the purification of fuel gas, coal gas, Claus-plant off-gases, chemical gases, process gases and other gases containing COS, and gases which are under pressure. Examples of gases which are under pressure are fuel gas (for example, 30 bar) and natural gas (for example, 70 bar).

As a consequence of the relatively high pH, less scrubbing liquid is needed than in known biological processes for the removal of sulphur compounds. The quantity of scrubbing liquid needed can further be reduced as a consequence of the presence of polythionate in the scrubbing liquid, which lowers the $H_2S/HS^-/S^{2-}/COS$ level in the liquid. The advantage in the case of purification of gases under pressure is also that, compared with known processes, relatively little scrubbing water is necessary and less energy therefore has to be expended on pressurising the scrubbing water.

The aerobic treatment of the sulphide-containing scrubbing liquid is preferably performed in such a way that the production of elemental sulphur is maximised. This can be achieved by using a limiting amount of oxygen, i.e. in particular 0.5–0.8 mole of $O_2$ per mole of $H_2S/HS^-$ or COS.

The bacteria that are capable of oxidising sulphide at a pH above 9 can for example be obtained from soda lakes, by known microbial enrichment and purification methods. The autotrophic sulphide-oxidising bacteria to be used according to the invention have one or more of the following characteristics:

Gram-negative bacteria from the β or γ subgroup of Proteobacteria;
Obligate autotrophs;
Capable of oxidising $HS^-$, $S^0$ and $S_2O_3^{2-}$;
pH optimum above 9.0, usually below 10.4, in particular around 9.5;
No growth on $H_2$ or $C_1$ compounds;
Not denitrifying, capable of assimilating $NO_2^-$ and/or $NO_3^-$ but not urea;
Temperature optimum between 24 and 37° C.;
Tolerance for NaCl and $Na_2CO_3/NaHCO_3$ up to at least 50 g/l each.

The following bacteria are representative examples of such autotrophic sulphide-oxidising bacteria.

Strain AL-2

This is a Gram-negative bacterium which can appear as anything from short rods to vibriods. It is motile by means of a single polar flagellum. On thiosulphate mineral salts agar with thiosulphate at pH 10, colonies can be up to 3 mm in diameter, round, convex and regular. With time they become white-yellow with deposited sulphur. Strain AL-2 may accumulate internal sulphur particles. It does not contain carboxysomes. Its DNA has a mol % GC ($T_m$) of 65.5. Preliminary results from 16S RNA analysis indicate that strain AL-2 belongs to the γ-subgroup of the Proteobacteria. Its genus is tentatively named as Thioalkalovibrio. Related genera are Thiomicrospira, Methylomicrobium and Methylococcus.

Strain AL-2 can oxidize $H_2S/HS^-$, $S^0$, $S_2O_3^{2-}$ and $S_4O_6^{2-}$. On $S_2O_3^{2-}$ it gives a yield of 8–9 mg dry weight per mmol substrate. It cannot grow on $H_2$ or $C_1$ compounds. It does not denitrify. It can use $NO_2^-$ and $NO_3^-$, but not $NH_4^+$, urea or organic nitrogen compounds, as its N-source.

Strain AL-2 has a pH range for growth between 8.0 and 10.4, with an optimum at about 9.5. It grows over the temperature range 10–39° C., with an optimum at about 28° C. It has a wide tolerance for NaCl (0–100 g/l) and sodium carbonates (0–150 g/l).

Strain AL-2 has been deposited in the Delft Culture Collection (an affiliate of the Centraal Bureau voor Schimmelcultures), Delft, NL, under accession number LMD 96.55, where it is accessible under the terms of the Budapest Treaty.

Strain AL-3

This is a Gram-negative rod. It is motile by means of 1–3 polar flagellae. On thiosulphate mineral salts agar with thiosulphate at pH 10, colonies can be up to 2 mm in diameter, round, convex, regular, pinkish and transparent, without accumulating sulphur. Strain AL-3 does not accumulate internal sulphur particles. It contains carboxysomes. Its DNA has a mol % GC ($T_m$) of 49.5. Preliminary results from 16S RNA analysis indicate that strain AL-3 belongs to the beta sub-group of the Proteobacteria. Its genus is tentatively named as Thioalkalobacter. Related genera are Thiomicrospira, Methylomicrobium and Methylococcus.

Strain AL-3 can oxidize $HS^-$, $S^0$ and $S_2O_3^{2-}$. On $S_2O_3^{2-}$ it gives a yield of 4–4.5 mg dry weight per mmol substrate. It cannot grow on $H_2$ or $C_1$ compounds. It does not denitrify. It can assimilate $NO_2^-$ and $NO_3^-$. $NH_4^+$ can also be (weakly) used as an N-source, but not urea or organic nitrogen compounds.

Strain AL-3 has a pH range for growth between 8.0 and 10.4, with an optimum at about 9.5. It grows over the temperature range 12–41° C., with an optimum at about 33° C. It has a wide tolerance for NaCl (0–70 g/l) and sodium carbonates (0–60 g/l).

Strain AL-3 has been deposited in the Delft Culture Collection under accession number LMD 95.63, where it is accessible under the terms of the Budapest Treaty. Other strains than AL-2 and AL-3 having essentially the same characteristics as either AL-2 or AL-3 and presumably belonging to the same genera have been isolated from different soda lakes.

A representative example of the alkaliphilic heterotrophic bacteria capable of oxidising thiosulphate is given below.

Strain ChG 3—3

Strain ChG 3—3 was isolated from a water column of the Black Sea. It is an obligate heterotroph.

Strain ChG 3—3 is a gram-negative, catalase-positive motile rod. It requires NaCl for growth. Strain ChG 3—3 was studied using standard taxonomic tests (API 20 NE), and compared to known species using an on-line database. Related genera are Pseudomonas, Deleya and Halomonas. Its nearest match was *Pseudomonas stutzeri* I sensu stricto (84.3% similarity). It is clearly a new species which, for the moment will be known as Pseudomonas strain ChG 3—3. It has a mol % G+C of 57.3.

Pseudomonas strain ChG 3—3 can grow over the pH range between 7.3 and 10.5, with an optimum around 8. It grows over a temperature range between 15 and 40° C., with an optimum around 20° C. It does not grow at 50° C. It requires carbonate, and will grow over a range from 0.2–0.8M.

Pseudomonas strain ChG 3—3 oxidizes $S_2O_3^{2-}$ to $S_4O_6^{2-}$, without gaining energy from the reaction. It requires the presence of an organic substrate (e.g. acetate) in order to do so.

Pseudomonas strain ChG 3—3 has been deposited in the Delft Culture Collection under accession number LMD 96.32, where it is accessible under the terms of the Budapest Treaty.

In the preferred configuration of the process using the thiosulphate-oxidising bacteria, the scrubbing liquid generally contains at least 10 μmol/l polythionate, preferably at least 100 μmol/l and, in particular, at least 1 mmol/l polythionate. For gases which are under pressure, i.e. have an increased pressure of at least 10 bar, in which case the scrubbing liquid therefore also has an increased pressure, the polythionate concentration is preferably at least 1 mmol/l, in particular at least 10 mmol/l and in special cases (pressures in the order of 100 bar or higher) 100 mmol/l or more. Where mention is made of polythionate concentration here, it is to be understood as meaning the concentration of trithionate and tetrathionate, including the concentration of thiosulphate: $[S_nO_6^{2-}]+\frac{1}{2}[S_2O_3^{2-}]$.

The thiosulphate is oxidised again into polythionate with the aid of the bacteria in accordance with the following reaction:

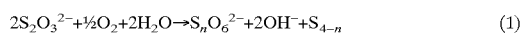

$$2S_2O_3^{2-}+\tfrac{1}{2}O_2+2H_2O \rightarrow S_nO_6^{2-}+2OH^-+S_{4-n} \qquad (1)$$

A cyclic process therefore results which, in principle, requires no topping-up of the thiosulphate/polythionate. If necessary, an initial concentration of thiosulphate can be obtained, or a replenishment of the thiosulphate concentration can be achieved, by oxidation of sulphide. The thiosulphate concentration at the beginning of, or during, the scrubbing process can therefore be increased by adding oxygen to the scrubbing liquid via the gas stream or in another way.

The reactions which probably play a role in the removal of $H_2S$ or COS, respectively, with the aid of polythionate are the following:

$$H_2S+OH^- \rightarrow SH^-+H_2O \qquad (2)$$

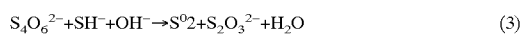

$$S_4O_6^{2-}+SH^-+OH^- \rightarrow S^0 2+S_2O_3^{2-}+H_2O \qquad (3)$$

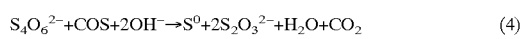

$$S_4O_6^{2-}+COS+2OH^- \rightarrow S^0+2S_2O_3^{2-}+H_2O+CO_2 \qquad (4)$$

Under alkaline conditions, tetrathionate further reacts as follows:

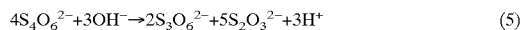

$$4S_4O_6^{2-}+3OH^- \rightarrow 2S_3O_6^{2-}+5S_2O_3^{2-}+3H^+ \qquad (5)$$

Trithionate reacts with $H_2S$ and COS:

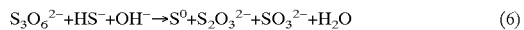

$$S_3O_6^{2-}+HS^-+OH^- \rightarrow S^0+S_2O_3^{2-}+SO_3^{2-}+H_2O \qquad (6)$$

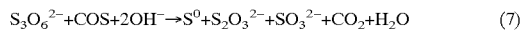

$$S_3O_6^{2-}+COS+2OH^- \rightarrow S^0+S_2O_3^{2-}+SO_3^{2-}+CO_2+H_2O \qquad (7)$$

Thiosulphate may also be formed by chemical autooxidation or biological oxidation of sulphide as follows:

$$2SH^-+2O_2 \rightarrow H_2O+S_2O_3^{2-} \qquad (8)$$

As a result of the presence of polythionate in the scrubbing liquid, $H_2S$ and COS are already effectively absorbed and converted in the gas scrubber by the reactions (2) and (3). Other sulphur compounds, such as carbon disulphide, alkyl mercaptans, dialkyl sulphides and dialkyl disulphides, in particular carbon disulphide and methyl mercaptan, can also be expediently be removed by scrubbing using the process according to the invention.

The autotrophic bacterial conversion of sulphide to sulphur is preferably carried out at a pH of above 9 up to 11, especially between 9.2 and 10.5. The optional heterotrophic bacterial conversion of thiosulphate into polythionate is preferably carried out at a pH of 9 to 12, in particular at a pH of 9.5–11 or even 10–11. If necessary, the pH is adjusted by adding caustic lye or soda. The bacteria are also able to use nitrogen oxides such as nitrate instead of oxygen in order to oxidise the thiosulphate. Usually, the medium contains a carbon source such as acetate or another organic substrate in order to enable bacterial growth.

Preferably, the scrubbing liquid has a pH of 8 to 11, in particular above 9 or even 9.5 to 10.5, at the instant of contact with the gases. The pH can be adjusted, if necessary, by adding a stream of water having a lower pH, for example a short-circuit stream of the cyclic process.

The formation of sulphur before and in the aerobic reactor results in a sulphur suspension which is drawn off. The sulphur is separated from said suspension and worked up by drying and eventual purification and can be reused.

Even if the gas to be purified contains, in addition to $H_2S$, other volatile sulphur compounds, such as small quantities of alkyl mercaptans or carbon disulphide, the spent scrubbing liquid containing the sulphur compounds can be introduced directly into the aerobic reactor with the sulphide-oxidising bacteria. If said reduced sulphur compounds are dissolved, they are referred to as "sulphide", but this term is also understood as meaning other reduced sulphur compounds, such as dissolved hydrogen sulphide ($H_2S$ or $HS^-$), disulphide, polysulphide, thiocarbonates, alkanethiolates and the like.

If the gas also contains $CO_2$, it will also be partially absorbed in the scrubbing liquid. The absorbed carbon dioxide in the form of bicarbonate will have a beneficial buffering action on the scrubbing liquid.

If the gas to be purified also contains carbon disulphide and/or carbonyl sulphide, it can expediently be removed by the process according to the invention. Absorbed COS and $CS_2$ are mainly converted to carbonate and sulphur in the aerobic reactor.

The gas scrubber to be used according to the invention can be of a conventional type provided an effective contact is brought about between the gas stream and the scrubbing liquid in the gas scrubber.

The aerobic reactors to be used according to the invention can be of any suitable type. Preferably, reactors of the vertical circulating type are used, such as those described, for example, in International Patent Application WO 94/29227, in which the gas to be used (in the aerobic reactor it is usually air) can provide the vertical circulation.

The invention also relates to an apparatus for carrying out the process as described above. Examples thereof are shown in the accompanying figures.

BRIEF DESCRIPTION OF THE DRAWINGS

FIG. 2 depicts another apparatus in which only one aerobic reactor is present.

DETAILED DESCRIPTION OF THE INVENTION

Figure 1:
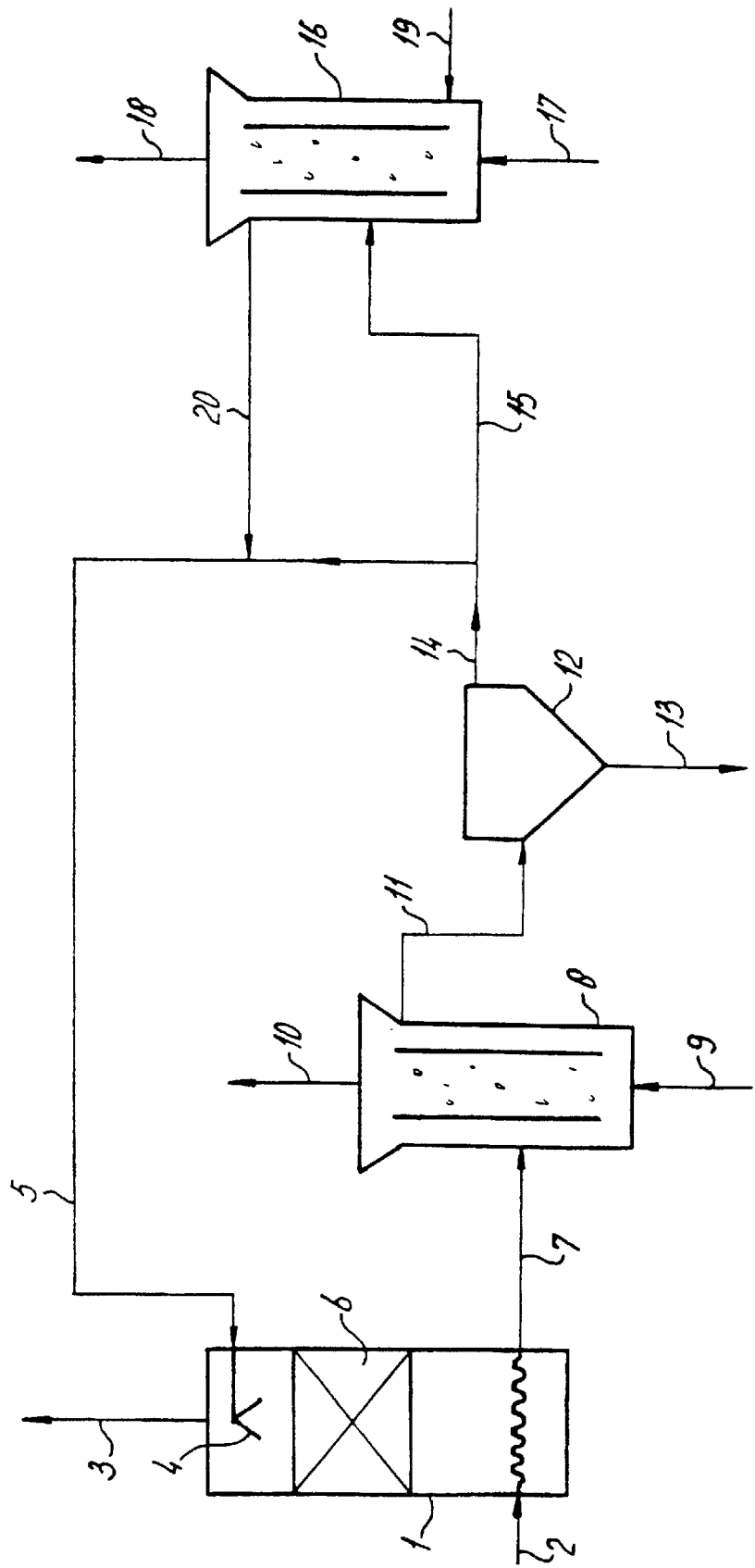
FIG. 1 depicts an apparatus for purifying gases containing $H_2S$ and/or COS using a combined autotrophic and heterotrophic aerobic treatment.

FIG. 1 shows an apparatus according to the invention for the purification of gases containing $H_2S$ and/or COS using a combined autotrophic and heterotrophic aerobic treatment. Gas scrubber 1 is provided with inlet line 2 for contaminated gas and outlet line 3 for purified gas. The gas scrubber contains a distributor device 4 for scrubbing liquid which is fed by recycle line 5, and a reaction zone 6, which ensures intensive contact between gas and liquid. Line 7 feeds loaded scrubbing liquid to aerobic reactor 8, which is provided with air from below in a controlled fashion via gas inlet 9. In aerobic reactor 8 sulphide is oxidised to elemental sulphur by sulphide-oxidising biomass. The spent air is removed via 10. The effluent from the aerobic reactor is passed to sulphur separator 12 via line 11. The separated sulphur slurry is removed via 13 and the treated effluent leaves the separator via 14 and some of it may be fed directly to recycle line 5. At least some of the effluent in 14 is fed via 15 to aerobic reactor 16, which is also provided with an air inlet 17 and a gas outlet 18. In aerobic reactor 16 thiosulphate is oxidised to polythionate by thiosulphate-oxidising biomass. An inlet line 19 for a nutrient source (for example, acetate) is also present. The effluent from the reactor is fed via 20 and the return line 5 back to the gas scrubber 1.

FIG. 2 shows a variant of this apparatus, in which only one aerobic reactor is present. This apparatus can be used for a process in which the gas to be purified contains relatively low concentrations of sulphur compounds and/or in which the aerobic treatment with autotrophic sulphide-oxidising bacteria yields only low levels of thiosulphate. The design of this apparatus is the same as that of FIG. 1, with omission of the second aerobic reactor containing thiosulphate-oxidising bacteria. Some of the scrubbing liquid can be fed back directly to the gas scrubber via short circuit 21.

The apparatus of FIG. 2 can also be used for a process in which the thiosulphate reactor is integrated with the sulphide reactor to form reactor 8. In this case, residual sulphide is oxidised therein to sulphur and thiosulphate is oxidised to polythionate. The chosen pH will be, for example, 9–10.

What is claimed is:

1. A process for removing hydrogen sulfide and/or carbonyl sulfide from a gas, which comprises:
   (a) scrubbing the gas with an aqueous scrubbing liquid having a pH of higher than 9.0 to obtain spent scrubbing liquid;
   (b) biologically treating the spent scrubbing liquid with sulfide-oxidizing bacteria in the presence of oxygen to produce elemental sulfur; said sulfide-oxidizing bacteria comprising autotrophic sulfide-oxidizing bacteria obtainable from soda lakes and having a pH optimum between 9.0 and 10.4; and
   (c) separating elemental sulfur from the biologically treated scrubbing liquid.

2. The process according to claim 1, wherein said scrubbing liquid has a pH of at least 9.5.

3. The process according to claim 1, wherein the treatment with sulfide-oxidizing bacteria is carried out at a pH between 9.2 and 10.5.

4. The process according to claim 1, wherein the gas containing hydrogen sulfide and/or carbonyl sulfide, also contains carbon disulfide and/or organic sulfur compounds.

5. A process for removing hydrogen sulfide and/or carbonyl sulfide from a gas, which comprises:
   (a) scrubbing the gas with an aqueous scrubbing liquid to obtain spent scrubbing liquid;
   (b) biologically treating the spent scrubbing liquid with sulfide-oxidizing bacteria in the presence of oxygen to produce elemental sulfur; said sulfide-oxidizing bacteria comprising obligate autotrophic sulfide-oxidizing bacteria capable of assimilating at least one of nitrate and nitrite; said bacteria being obtainable from soda lakes and having a pH optimum between 9.0 and 10.4; and (c) separating elemental sulfur from the biologically treated scrubbing liquid.

6. The process according to claim 5, wherein said obligate autotrophic bacteria are selected from the genera Thioalcalovibrio and Thioalcalobacterium.

7. The process according to claim 5, wherein said scrubbing liquid has a pH of higher than 9.0.

8. The process according to claim 5, wherein the treatment with sulfide-oxidizing bacteria is carried out at a pH between 9.2 and 10.5.

9. The process according to claim 5, wherein the gas containing hydrogen sulfide and/or carbonyl sulfide, also contains carbon disulfide and/or organic sulfur compounds.

10. A process for removing hydrogen sulfide and/or carbonyl sulfide from a gas, which comprises:
   (a) scrubbing the gas with an aqueous scrubbing liquid to obtain spent scrubbing liquid;
   (b) biologically treating the spent scrubbing liquid with sulfide-oxidizing bacteria in the presence of oxygen to produce elemental sulfur; said sulfide-oxidizing bacteria comprising autotrophic sulfide-oxidizing bacteria obtainable from soda lakes and having a pH optimum between 9.0 and 10.4;
   (c) separating elemental sulfur from the biologically treated scrubbing liquid; and
   (d) further treating the biologically treated scrubbing liquid of step (b) with thiosulfate-oxidizing bacteria, and subsequently returning the biologically treated scrubbing liquid to the scrubbing step (a).

11. The process according to claim 10, wherein said thiosulfate-oxidizing bacteria are heterotrophic bacteria.

12. The process according to claim 11, wherein said heterotrophic bacteria comprise Pseudomonas-related bacteria.

13. The process according to claim 12, wherein said heterotrophic bacteria comprise bacteria denoted herein as ChG3—3.

14. The process according to claim 10, wherein the treatment with thiosulfate-oxidizing bacteria is carried out at a pH of 9 or higher.

15. The process according to claim 10, wherein the treatment with thiosulfate-oxidizing bacteria is carried out at a pH of 9.5–11.

16. The process according to claim 10, wherein the treatment with thiosulfate-oxidizing bacteria is carried out subsequently to the treatment with sulfide-oxidizing bacteria.

17. The process according to claim 10, wherein the scrubbing liquid treated with said thiosulfate-oxidizing bacteria contains at least 100 $\mu$mol/l of trithionate and/or tetrathionate.

18. The process according to claim 10, wherein said scrubbing liquid has a pH of higher than 9.0.

19. The process according to claim 10, wherein the gas containing hydrogen sulfide and/or carbonyl sulfide, also contains carbon disulfide and/or organic sulfur compounds.

* * * * *